US005866330A

United States Patent [19]
Kinzler et al.

[11] Patent Number: 5,866,330
[45] Date of Patent: *Feb. 2, 1999

[54] METHOD FOR SERIAL ANALYSIS OF GENE EXPRESSION

[75] Inventors: Kenneth W. Kinzler, Bel Air; Bert Vogelstein, Baltimore; Victor E. Velculescu, Baltimore; Lin Zhang, Baltimore, all of Md.

[73] Assignee: The Johns Hopkins University School of Medicine, Baltimore, Md.

[ * ] Notice: The term of this patent shall not extend beyond the expiration date of Pat. No. 5,695,937.

[21] Appl. No.: 544,861

[22] Filed: Oct. 18, 1995

Related U.S. Application Data

[63] Continuation-in-part of Ser. No. 527,154, Sep. 12, 1995, Pat. No. 5,695,937.

[51] Int. Cl.$^6$ .............................. C12Q 1/68; C12P 19/34; C07H 21/02; C07H 21/04
[52] U.S. Cl. ............................ 435/6; 435/91.2; 536/23.1; 536/24.3; 536/24.33
[58] Field of Search .................................. 435/6, 5, 91.2; 536/23.1, 24.3, 24.33

[56] References Cited

U.S. PATENT DOCUMENTS 5,508,169   4/1996   Deugau et al. ............................. 435/6

FOREIGN PATENT DOCUMENTS

| 0 679 716 A1 | 2/1995 | European Pat. Off. . |
| WO 93/00353 | 1/1993 | WIPO . |
| WO 93/16178 | 8/1993 | WIPO . |
| WO 94/16092 | 7/1994 | WIPO . |
| WO 95/20681 | 8/1995 | WIPO . |
| WO 95/21944 | 8/1995 | WIPO . |
| WO 95/27080 | 10/1995 | WIPO . |

OTHER PUBLICATIONS

Unrau and Deugau , Gene 145: 163–169, 1994.
White et al., Anal. Biochem. 199: 184–'90, 1991.
Sambrook et al. Molecular Cloning: A Laboratory Munual, vol. 2, 8.27–8.29, vol. 3, F.8,F.11, 1989.
Liu, et al., *Large–Scale Cloning of Human Chromosome 2–specific Yeast Artificial Chromosomes (YACs) Using an Interspersed Repetitive Sequences (IRS)–PCR Approach*, Genomics, 26:178, 1995.
Carney, et al., *Random rapid amplification of cDNA ends (RRACE)allows for cloning of multiple novel human cDNA fragments containing (CAG)n repeats*, Gene, 155:289, 1995.
Munroe, et al., *Systematic screening of an arrayed cDNA Library by PCR*, Proc. Natl. Acad. Sci., USA, 92:2209, 1995.
Okubo, et al., *Large Scale cDNA sequencing for analysis of quantitative and qualitative aspects of gene expression*, Nature Genetics, 2:173, 1992.
Adams, et al., *Sequence identification of 2,375 human brain genes*, Nature, 355:632, 1992.
Fields, et al., *How many genes in the human genome?*, Nature Genetics, 7:345, 1994.
Olson, et al.,*A Common Language for Physical Mapping of the Human Genome*, Science, 245:1434, 1989.
Altschul, et al., Basic Local Alignment Search Tool, J. of Molecular Biology, 213(1):403, 1990.
Liang and Pardee, *Differential Display of Eukaryotic Messenger RNA by Means of the Polymerase Chain Reaction*, Science, 257:967, 1992.
Ivanova and Belyavsky, *Identification of differentially expressed genes by restriction endonuclease–based gene expression fingerprinting*, Nucleic Acids Research, 23(15):2954, 1995.
Prashar and Weissman, *Analysis of differential gene expression by display of 3' end restriction fragments of cDNAs*, Proc. Natl. Acad. Sci. USA, 93:659, 1996.
Sambrook, et al., Alternative Methods of Cloning cDNA, *Molecular Cloning, A Laboratory Manual*, 1989 2:8.27–8.29 (Second edition, New York, Cold Spring Harbor Laboratory Press).
Sambrook, et al., Ligation of phosphorylated linkers to blunt–ended target fragments, *Molecular Cloning, A Laboratory Manual*, 1989, 3:F.9–F.11 (Second edition, New York, Cold Spring Harbor Laboratory Press).
Unrau, et al., Non–cloning amplification of specific DNA fragments from whole genomic DNA digests using DNA 'indexers', Gene, 1994, 145:163–169.
White, et al., Concatemer Chain Reaction: A Taq DNA Polymerase–Mediated Mechanism for Generating Long Tandemly Repetitive DNA Sequences, *Analytical Biochemistry*, 1991, 199:184–190.
Kato, Kikuya, Description of the entire mRNA population by a 3' end cDNA fragment generated by class IIS restriction enzymes, Nucleic Acids Research, 1995, 23:3685–3690.
Adams et al., "Complementary DNA Sequencing: Expressed Sequence Tags and Human Genome Project", Science, 1991, 252, 1651–1656.
Adams et al., "Sequence identification of 2,375 human brain genes," Nature, 1992, 355, 632–634.
Okubo et al., "Large scale cDNA sequencing for analysis of quantitative and qualitative aspects of gene expression," Nature Genetics, 1992, 2, 173–179.
Velculescu et al., "Serial Analysis of Gene Expression", Science, 1995, 270, 484–487.
Adams, "Serial analysis of gene expression: ESTs get smaller", Bioessays, 1996, 18(4), 261–262.

*Primary Examiner*—Stephanie W. Zitomer
*Attorney, Agent, or Firm*—Fish & Richardson P.C.

[57] ABSTRACT

Serial analysis of gene expression, SAGE, a method for the rapid quantitative and qualitative analysis of transcripts is provided. Short defined sequence tags corresponding to expressed genes are isolated and analyzed. Sequencing of over 1,000 defined tags in a short period of time (e.g., hours) reveals a gene expression pattern characteristic of the function of a cell or tissue. Moreover, SAGE is useful as a gene discovery tool for the identification and isolation of novel sequence tags corresponding to novel transcripts and genes.

44 Claims, 5 Drawing Sheets

P1

P2

METHOD FOR SERIAL ANALYSIS OF GENE EXPRESSION

This application is a continuation-in-part application of Serial No. 08/527,154, filed Sep. 12, 1995 now U.S. Pat. No. 5,695,937.

This invention was made with support from National Institutes of Health Grant Nos. CA57345, CA35494, and GM07309. The Government has certain rights in this invention.

FILED OF THE INVENTION

The present invention relates generally to the field of gene expression and specifically to a method for the serial analysis of gene expression (SAGE) for the analysis of a large number of transcripts by identification of a defined region of a transcript which corresponds to a region of an expressed gene.

BACKGROUND OF THE INVENTION

Determination of the genomic sequence of higher organisms, including humans, is now a real and attainable goal. However, this analysis only represents one level of genetic complexity. The ordered and timely expression of genes represents another level of complexity equally important to the definition and biology of the organism.

The role of sequencing complementary DNA (cDNA), reverse transcribed from mRNA, as part of the human genome project has been debated as proponents of genomic sequencing have argued the difficulty of finding every mRNA expressed in all tissues, cell types, and developmental stages and have pointed out that much valuable information from intronic and intergenic regions, including control and regulatory sequences, will be missed by cDNA sequencing (Report of the Committee on Mapping and Sequencing the Human Genome, National Academy Press, Washington, D.C., 1988). Sequencing of transcribed regions of the genome using cDNA libraries has heretofore been considered unsatisfactory. Libraries of cDNA are believed to be dominated by repetitive elements, mitochondrial genes, ribosomal RNA genes, and other nuclear genes comprising common or housekeeping sequences. It is believed that cDNA libraries do not provide all sequences corresponding to structural and regulatory polypeptides or peptides (Putney, et al., *Nature*, 302:718, 1983).

Another drawback of standard cDNA cloning is that some mRNAs are abundant while others are rare. The cellular quantities of mRNA from various genes can vary by several orders of magnitude.

Techniques based on cDNA subtraction or differential display can be quite useful for comparing gene expression differences between two cell types (Hedrick, et al., *Nature*, 308:149, 1984; Liang and Pardee, *Science*, 257:967, 1992), but provide only a partial analysis, with no direct information regarding abundance of messenger RNA. The expressed sequence tag (EST) approach has been shown to be a valuable tool for gene discovery (Adams, et al., *Science* 252:1656, 1991; Adams, et al., *Nature*, 355:632, 1992; Okubo et al., *Nature Genetics*, 2:173, 1992), but like Northern blotting, RNase protection, and reverse transcriptase-polymerase chain reaction (RT-PCR) analysis (Alwine, et al., *Proc. Natl. Acad Sci, U.S.A.*, 74:5350, 1977; Zinn et al, *Cell*, 34:865, 1983; Veres, et al., *Science*, 237:415, 1987), only evaluates a limited number of genes at a time. In addition, the EST approach preferably employs nucleotide sequences of 150 base pairs or longer for similarity searches and mapping.

Sequence tagged sites (STSs) (Olson, et al., *Science*, 245:1434, 1989) have also been utilized to identify genomic markers for the physical mapping of the genome. These short sequences from physically mapped clones represent uniquely identified map positions in the genome. In contrast, the identification of expressed genes relies on expressed sequence tags which are markers for those genes actually transcribed and expressed in vivo.

There is a need for an improved method which allows rapid, detailed analysis of thousands of expressed genes for the investigation of a variety of biological applications, particularly for establishing the overall pattern of gene expression in different cell types or in the same cell type under different physiologic or pathologic conditions. Identification of different patterns of expression has several utilities, including the identification of appropriate therapeutic targets, candidate genes for gene therapy (e.g., gene replacement), tissue typing, forensic identification, mapping locations of disease-associated genes, and for the identification of diagnostic and prognostic indicator genes.

SUMMARY OF THE INVENTION

The present invention provides a method for the rapid analysis of numerous transcripts in order to identify the overall pattern of gene expression in different cell types or in the same cell type under different physiologic, developmental or disease conditions. The method is based on the identification of a short nucleotide sequence tag at a defined position in a messenger RNA. The tag is used to identify the corresponding transcript and gene from which it was transcribed. By utilizing dimerized tags, termed a "ditag", the method of the invention allows elimination of certain types of bias which might occur during cloning and/or amplification and possibly during data evaluation. Concatenation of these short nucleotide sequence tags allows the efficient analysis of transcripts in a serial manner by sequencing multiple tags on a single DNA molecule, for example, a DNA molecule inserted in a vector or in a single clone.

The method described herein is the serial analysis of gene expression (SAGE), a novel approach which allows the analysis of a large number of transcripts. To demonstrate this strategy, short cDNA sequence tags were generated from mRNA isolated from pancreas, randomly paired to form ditags, concatenated, and cloned. Manual sequencing of 1,000 tags revealed a gene expression pattern characteristic of pancreatic function. Identification of such patterns is important diagnostically and therapeutically, for example. Moreover, the use of SAGE as a gene discovery tool was documented by the identification and isolation of new pancreatic transcripts corresponding to novel tags. SAGE provides a broadly applicable means for the quantitative cataloging and comparison of expressed genes in a variety of normal, developmental, and disease states.

DESCRIPTION OF THE PREFERRED EMBODIMENTS

Figure 1A:
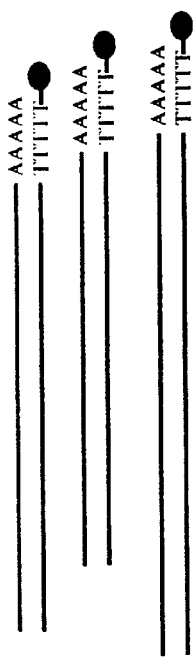
FIG. 1 shows a schematic of SAGE. The first restriction enzyme, or anchoring enzyme, is NlaIII and the second enzyme, or tagging enzyme, is FokI in this example. Sequences represent primer derived sequences, and transcript derived sequences with "X" and "O" representing nucleotides of different tags.
Figure 1A:
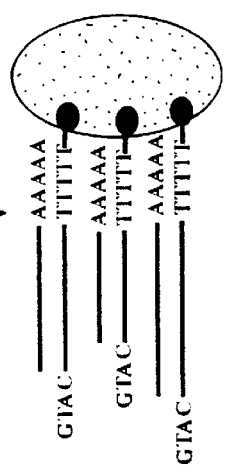
Figure 1A:
Figure 1A:
Figure 1B:
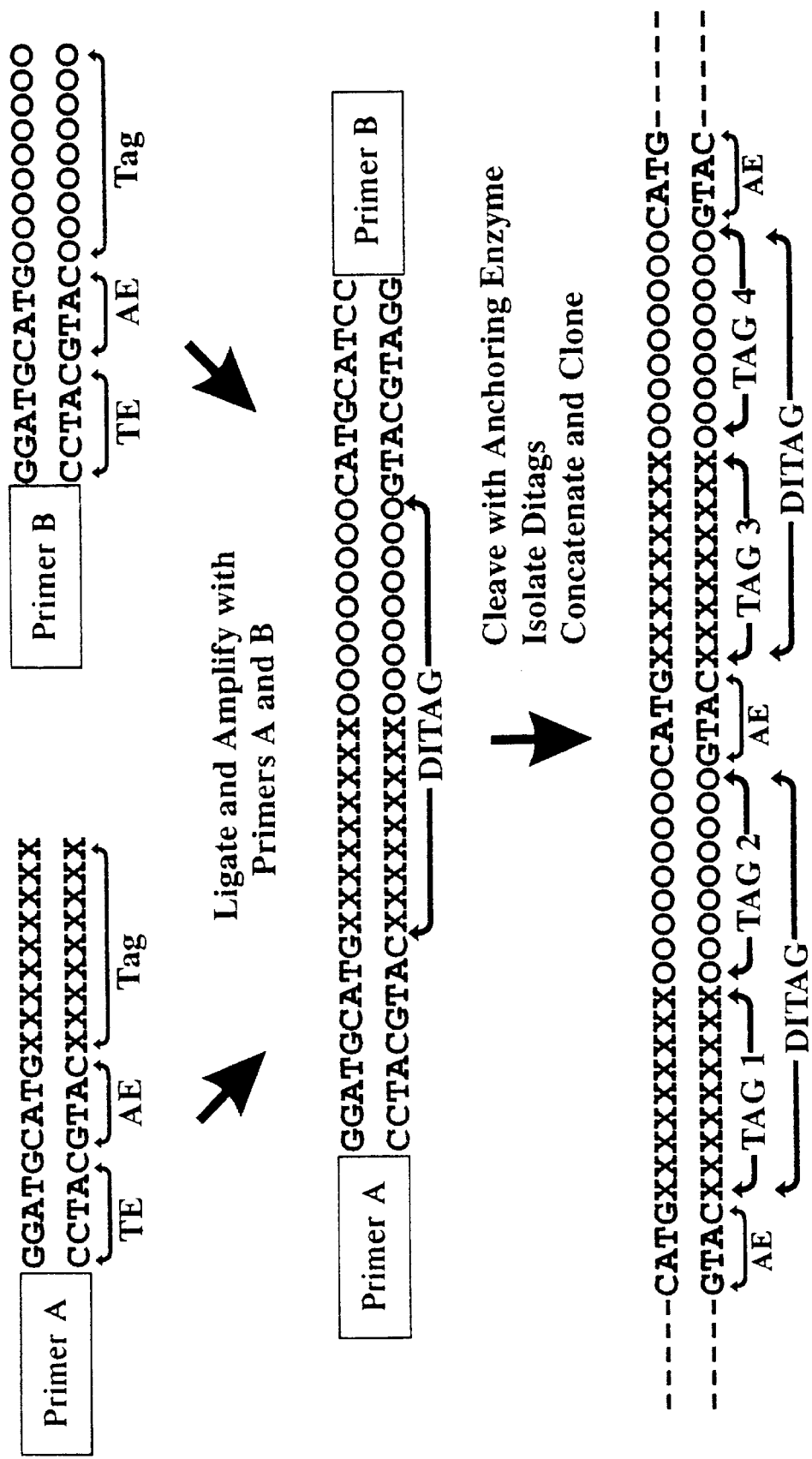

The present invention provides a rapid, quantitative process for determining the abundance and nature of transcripts corresponding to expressed genes. The method, termed serial analysis of gene expression (SAGE), is based on the identification of and characterization of partial, defined sequences of transcripts corresponding to gene segments. These defined transcript sequence "tags" are markers for genes which are expressed in a cell, a tissue, or an extract, for example.

SAGE is based on several principles. First, a short nucleotide sequence tag (9 to 10 bp) contains sufficient information content to uniquely identify a transcript provided it is isolated from a defined position within the transcript. For example, a sequence as short as 9 bp can distinguish 262,144 transcripts ($4^9$) given a random nucleotide distribution at the tag site, whereas estimates suggest that the human genome encodes about 80,000 to 200,000 transcripts (Fields, et al., *Nature Genetics,* 7:345 1994). The size of the tag can be shorter for lower eukaryotes or prokaryotes, for example, where the number of transcripts encoded by the genome is lower. For example, a tag as short as 6–7 bp may be sufficient for distinguishing transcripts in yeast.

Second, random dimerization of tags allows a procedure for reducing bias (caused by amplification and/or cloning). Third, concatenation of these short sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. All of these principles may be applied independently, in combination, or in combination with other known methods of sequence identification.

In a first embodiment, the invention provides a method for the detection of gene expression in a particular cell or tissue, or cell extract, for example, including at a particular developmental stage or in a particular disease state. The method comprises producing complementary deoxyribonucleic acid (cDNA) oligonucleotides, isolating a first defined nucleotide sequence tag from a first cDNA oligonucleotide and a second defined nucleotide sequence tag from a second cDNA oligonucleotide, linking the first tag to a first oligonucleotide linker, wherein the first oligonucleotide linker comprises a first sequence for hybridization of an amplification primer and linking the second tag to a second oligonucleotide linker, wherein the second oligonucleotide linker comprises a second sequence for hybridization of an amplification primer, and determining the nucleotide sequence of the tag(s), wherein the tag(s) correspond to an expressed gene.

FIG. 1 shows a schematic representation of the analysis of messenger RNA (mRNA) using SAGE as described in the method of the invention. mRNA is isolated from a cell or tissue of interest for in vitro synthesis of a double-stranded DNA sequence by reverse transcription of the mRNA. The double-stranded DNA complement of mRNA formed is referred to as complementary (cDNA).

The term "oligonucleotide") as used herein refers to primers or oligomer fragments comprised of two or more deoxyribonucleotides or ribonucleotides, preferably more than three. The exact size will depend on many factors, which in turn depend on the ultimate function or use of the oligonucleotide.

The method further includes ligating the first tag linked to the first oligonucleotide linker to the second tag linked to the second oligonucleotide linker and forming a "ditag". Each ditag represents two defined nucleotide sequences of at least one transcript, representative of at least one gene. Typically, a ditag represents two transcripts from two distinct genes. The presence of a defined cDNA tag within the ditag is indicative of expression of a gene having a sequence of that tag.

The analysis of ditags, formed prior to any amplification step, provides a means to eliminate potential distortions introduced by amplification, e.g., PCR. The pairing of tags for the formation of ditags is a random event. The number of different tags is expected to be large, therefore, the probability of any two tags being coupled in the same ditag is small, even for abundant transcripts. Therefore, repeated ditags potentially produced by biased standard amplification and/or cloning methods are excluded from analysis by the method of the invention.

The term "defined" nucleotide sequence, or "defined" nucleotide sequence tag, refers to a nucleotide sequence derived from either the 5' or 3' terminus of a transcript. The sequence is defined by cleavage with a first restriction endonuclease, and represents nucleotides either 5' or 3' of the first restriction endonuclease site, depending on which terminus is used for capture (e.g., 3' when oligo-dT is used for capture as described herein).

As used herein, the terms "restriction endonucleases" and "restriction enzymes" refer to bacterial enzymes which bind to a specific double-stranded DNA sequence termed a recognition site or recognition nucleotide sequence, and cut double-stranded DNA at or near the specific recognition site.

The first endonuclease, termed "anchoring enzyme" or "AE" in FIG. 1, is selected by its ability to cleave a transcript at least one time and therefore produce a defined sequence tag from either the 5' or 3' end of a transcript. Preferably, a restriction endonuclease having at least one recognition site and therefore having the ability to cleave a majority of cDNAs is utilized. For example, as illustrated herein, enzymes which have a 4 base pair recognition site are expected to cleave every 256 base pairs ($4^4$) on average while most transcripts are considerably larger. Restriction endonucleases which recognize a 4 base pair site include NlaIII, as exemplified in the EXAMPLES of the present invention. Other similar endonucleases having at least one recognition site within a DNA molecule (e.g., cDNA) will be known to those of skill in the art (see for example, *Current Protocols in Molecular Biology,* Vol. 2, 1995, Ed. Ausubel, et al., Greene Publish. Assoc. & Wiley Interscience, Unit 3.1.15; New England Biolabs Catalog, 1995).

After cleavage with the anchoring enzyme, the most 5' or 3' region of the cleaved cDNA can then be isolated by binding to a capture medium. For example, as illustrated in the present EXAMPLES, streptavidin beads are used to isolate the defined 3' nucleotide sequence tag when the oligo dT primer for cDNA synthesis is biotinylated. In this example, cleavage with the first or anchoring enzyme provides a unique site on each transcript which corresponds to the restriction site located closest to the poly-A tail. Likewise, the 5' cap of a transcript (the cDNA) can be utilized for labeling or binding a capture means for isolation of a 5' defined nucleotide sequence tag. Those of skill in the art will know other similar capture systems (e.g., biotin/streptavidin, digoxigenin/anti-digoxigenin) for isolation of the defined sequence tag as described herein. The invention is not limited to use of a single "anchoring" or first restriction endonuclease. It may be desirable to perform the method of the invention sequentially, using different enzymes on separate samples of a preparation, in order to identify a complete pattern of transcription for a cell or tissue. In addition, the use of more than one anchoring enzyme provides confirmation of the expression pattern obtained from the first anchoring enzyme. Therefore, it is also envisioned that the first or anchoring endonuclease may rarely cut cDNA such that few or no cDNA representing abundant transcripts are cleaved. Thus, transcripts which are cleaved represent "unique" transcripts. Restriction enzymes that have a 7–8 bp recognition site for example, would be enzymes that would rarely cut cDNA. Similarly, more than one tagging enzyme, described below, can be utilized in order to identify a complete pattern of transcription.

The term "isolated" as used herein includes polynucleotides substantially free of other nucleic acids, proteins, lipids, carbohydrates or other materials with which it is naturally associated. cDNA is not naturally occurring as such, but rather is obtained via manipulation of a partially purified naturally occurring mRNA. Isolation of a defined sequence tag refers to the purification of the 5' or 3' tag from other cleaved cDNA.

In one embodiment, the isolated defined nucleotide sequence tags are separated into two pools of cDNA, when the linkers have different sequences. Each pool is ligated via the anchoring, or first restriction endonuclease site to one of two linkers. When the linkers have the same sequence, it is not necessary to separate the tags into pools. The first oligonucleotide linker comprises a first sequence for hybridization of an amplification primer and the second oligonucleotide linker comprises a second sequence for hybridization of an amplification primer. In addition, the linkers further comprise a second restriction endonuclease site, also termed the "tagging enzyme" or "TE". The method of the invention does not require, but preferably comprises amplifying the ditag oligonucleotide after ligation.

The second restriction endonuclease cleaves at a site distant from or outside of the recognition site. For example, the second restriction endonuclease can be a type IIS restriction enzyme. Type IIS restriction endonucleases cleave at a defined distance up to 20 bp away from their asymmetric recognition sites (Szybalski, W., *Gene,* 40:169, 1985). Examples of type IIS restriction endonucleases include BsmFI and FokI. Other similar enzymes will be known to those of skill in the art (see, *Current Protocols in Molecular Biology,* supra).

The first and second "linkers" which are ligated to the defined nucleotide sequence tags are oligonucleotides having the same or different nucleotide sequences. For example, the linkers illustrated in the Examples of the present invention include linkers having different sequences:

5'-TTTTACCAGCTTATTCAATTCGGTCCTCTCGCA-CAGGGACATG-3' (SEQ ID NO:1)
3'-ATGGTCGAATAAGTTAAGCCAGGAGAGC-GTGTCCCT-5' (SEQ ID NO:2)
and
5'-TTTTTGTAGACATTCTAGTATCTCGTCAAGTCG-GAAGGGACATG-3' (SEQ ID NO:3)
3'-AACATCTGTAAGATCATAGAGCAGTTCA-GCCTTCCCT-5' (SEQ ID NO:4), wherein A is a dideoxy nucleotide (e.g., dideoxy A). Other similar linkers can be utilized in the method of the invention; those of skill in the art can design such alternate linkers.

The linkers are designed so that cleavage of the ligation products with the second restriction enzyme, or tagging enzyme, results in release of the linker having a defined nucleotide sequence tag (e.g., 3' of the restriction endonuclease cleavage site as exemplified herein). The defined nucleotide sequence tag may be from about 6 to 30 base pairs. Preferably, the tag is about 9 to 11 base pairs. Therefore, a ditag is from about 12 to 60 base pairs, and preferably from 18 to 22 base pairs.

The pool of defined tags ligated to linkers having the same sequence, or the two pools of defined nucleotide sequence tags ligated to linkers having different nucleotide sequences, are randomly ligated to each other "tail to tail". The portion of the cDNA tag furthest from the linker is referred to as the "tail". As illustrated in FIG. 1, the ligated tag pair, or ditag, has a first restriction endonuclease site upstream (5') and a first restriction endonuclease site downstream (3') of the ditag; a second restriction endonuclease cleavage site upstream and downstream of the ditag, and a linker oligonucleotide containing both a second restriction enzyme recognition site and an amplification primer hybridization site upstream and downstream of the ditag. In other words, the ditag is flanked by the first restriction endonuclease site, the second restriction endonuclease cleavage site and the linkers, respectively.

The ditag can be amplified by utilizing primers which specifically hybridize to one strand of each linker. Preferably, the amplification is performed by standard polymerase chain reaction (PCR) methods as described (U.S. Pat. No. 4,683,195). Alternatively, the ditags can be amplified by cloning in prokaryotic-compatible vectors or by other amplification methods known to those of skill in the art.

The term "primer" as used herein refers to an oligonucleotide, whether occurring naturally or produced synthetically, which is capable of acting as a point of initiation of synthesis when placed under conditions in which synthesis of primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. In the present invention, the primers are substantially complementary to the oligonucleotide linkers.

Primers useful for amplification of the linkers exemplified herein as SEQ ID NO:1–4 include 5'-CCAGCTTATTCAATTCGGTCC-3' (SEQ ID NO:5) and 5'-GTAGACATTCTAGTATCTCGT-3' (SEQ ID NO:6). Those of skill in the art can prepare similar primers for amplification based on the nucleotide sequence of the linkers without undue experimentation.

Cleavage of the amplified PCR product with the first restriction endonuclease allows isolation of ditags which can be concatenated by ligation. After ligation, it may be desirable to clone the concatemers, although it is not required in the method of the invention. Analysis of the ditags or concatemers, whether or not amplification was performed, is by standard sequencing methods. Concatemers generally consist of about 2 to 200 ditags and preferably from about 8 to 20 ditags. While these are preferred concatemers, it will be apparent that the number of ditags which can be concatenated will depend on the length of the individual tags and can be readily determined by those of skill in the art without undue experimentation. After formation of concatemers, multiple tags can be cloned into a vector for sequence analysis, or alternatively, ditags or concatemers can be directly sequenced without cloning by methods known to those of skill in the art.

Among the standard procedures for cloning the defined nucleotide sequence tags of the invention is insertion of the tags into vectors such as plasmids or phage. The ditag or concatemers of ditags produced by the method described herein are cloned into recombinant vectors for further analysis, e.g., sequence analysis, plaque/plasmid hybridization using the tags as probes, by methods known to those of skill in the art.

The term "recombinant vector" refers to a plasmid, virus or other vehicle known in the art that has been manipulated by insertion or incorporation of the ditag genetic sequences. Such vectors contain a promoter sequence which facilitates the efficient transcription of the a marker genetic sequence for example. The vector typically contains an origin of replication, a promoter, as well as specific genes which allow phenotypic selection of the transformed cells. Vectors suitable for use in the present invention include for example, pBlueScript (Stratagene, La Jolla, Calif.); pBC, pSL301 (Invitrogen) and other similar vectors known to those of skill in the art. Preferably, the ditags or concatemers thereof are ligated into a vector for sequencing purposes.

Vectors in which the ditags are cloned can be transferred into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

Transformation of a host cell with a vector containing ditag(s) may be carried out by conventional techniques as are well known to those skilled in the art. Where the host is prokaryotic, such as *E. Coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed by electroporation or other commonly used methods in the art.

The ditags present in a particular clone can be sequenced by standard methods (see for example, *Current Protocols in Molecular Biology*, supra, Unit 7) either manually or using automated methods.

In another embodiment, the present invention provides a kit useful for detection of gene expression wherein the presence of a defined nucleotide tag or ditag is indicative of expression of a gene having a sequence of the tag, the kit comprising one or more containers comprising a first container containing a first oligonucleotide linker having a first sequence useful hybridization of an amplification primer; a second container containing a second oligonucleotide linker having a second oligonucleotide linker having a second sequence useful hybridization of an amplification primer, wherein the linkers further comprise a restriction endonuclease site for cleavage of DNA at a site distant from the restriction endonuclease recognition site; and a third and fourth container having a nucleic acid primers for hybridization to the first and second unique sequence of the linker. It is apparent that if the oligonucleotide linkers comprise the same nucleotide sequence, only one container containing linkers is necessary in the kit of the invention.

In yet another embodiment, the invention provides an oligonucleotide composition having at least two defined nucleotide sequence tags, wherein at least one of the sequence tags corresponds to at least one expressed gene. The composition consists of about 1 to 200 ditags, and preferably about 8 to 20 ditags. Such compositions are useful for the analysis of gene expression by identifying the defined nucleotide sequence tag corresponding to an expressed gene in a cell, tissue or cell extract, for example.

It is envisioned that the identification of differentially expressed genes using the SAGE technique of the invention can be used in combination with other genomics techniques. For example, individual tags, and preferably ditags, can be hybridized with oligonucleotides immobilized on a solid support (e.g., nitrocellulose filter, glass slide, silicon chip). Such techniques include "parallel sequence analysis" or PSA, as described below. The sequence of the ditags formed by the method of the invention can also be determined using limiting dilutions by methods including clonal sequencing (CS).

Briefly, PSA is performed after ditag preparation, wherein the oligonucleotide sequences to which the ditags are hybridized are preferably unlabeled and the ditag is preferably detectably labeled. Alternatively, the oligonucleotide can be labeled rather than the ditag. The ditags can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the ditag, or will be able to ascertain such, using routine experimentation. For example, PCR can be performed with labeled (e.g., fluorescein tagged) primers. Preferably, the ditag contains a fluorescent end label.

The labeled or unlabeled ditags are separated into single-stranded molecules which are preferably serially diluted and added to a solid support (e.g., a silicon chip as described by Fodor, et al., *Science,* 251:767, 1991) containing oligonucleotides representing, for example, every possible permutation of a 10-mer (e.g., in each grid of a chip). The solid support is then used to determine differential expression of the tags contained within that support (e.g., on a grid on a chip) by hybridization of the oligonucleotides on the solid support with tags produced from cells under different conditions (e.g., different stage of development, growth of cells in the absence and presence of a growth factor, normal versus transformed cells, comparison of different tissue expression, etc). In the case of fluoresceinated end labeled ditags, analysis of fluorescence is indicative of hybridization to a particular 10-mer. When the immobilized oligonucleotide is fluoresceinated for example, a loss of fluorescence due to quenching (by the proximity of the hybridized ditag to the labeled oligo) is observed and is analyzed for the pattern of gene expression. An illustrative example of the method is shown in Example 4 herein.

The SAGE method of the invention is also useful for clonal sequencing, similar to limiting dilution techniques used in cloning of cell lines. For example, ditags or concatemers thereof, are diluted and added to individual receptacles such that each receptacle contains less than one DNA molecule per receptacle. DNA in each receptacle is amplified and sequenced by standard methods known in the art, including mass spectroscopy. Assessment of differential expression is performed as described above for SAGE.

Those of skill in the art can readily determine other methods of analysis for ditags or individual tags produced by SAGE as described in the present invention, without resorting to undue experimentation.

The concept of deriving a defined tag from a sequence in accordance with the present invention is useful in matching tags of samples to a sequence database. In the preferred embodiment, a computer method is used to match a sample sequence with known sequences.

In one embodiment, a sequence tag for a sample is compared to corresponding information in a sequence database to identify known sequences that match the sample sequence. One or more tags can be determined for each sequence in the sequence database as the N base pairs adjacent to each anchoring enzyme site within the sequence. However, in the preferred embodiment, only the first anchoring enzyme site from the 3' end is used to determine a tag. In the preferred embodiment, the adjacent base pairs defining a tag are on the 3' side of the anchoring enzyme site, and N is preferably 9.

A linear search through such a database may be used. However, in the preferred embodiment, a sequence tag from a sample is converted to a unique numeric representation by converting each base pair (A, C, G, or T) of an N-base tag to a number or "tag code" (e.g., A=0, C=1, G=2, T=3, or any other suitable mapping). A tag is determined for each sequence of a sequence database as described above, and the tag is converted to a tag code in a similar manner. In the preferred embodiment, a set of tag codes for a sequence database is stored in a pointer file. The tag code for a sample sequence is compared to the tag codes in the pointer file to determine the location in the sequence database of the sequence corresponding to the sample tag code. (Multiple corresponding sequences may exist if the sequence database has redundancies).

Figure 4:
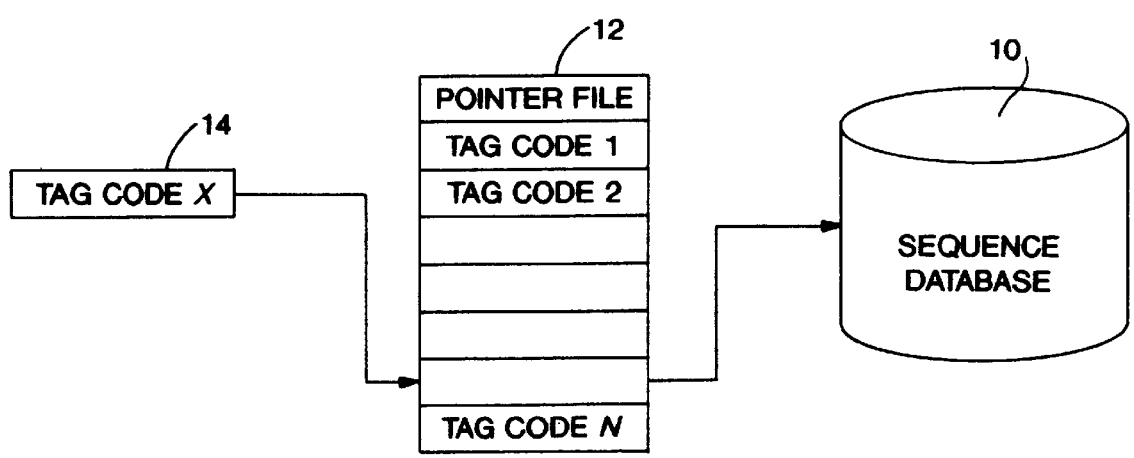
FIG. 4 is a block diagram of a tag code database access system in accordance with the present invention.

FIG. 4 is a block diagram of a tag code database access system in accordance with the present invention. A sequence database 10 (e.g., the Human Genome Sequence Database) is processed as described above, such that each sequence has a tag code determined and stored in a pointer file 12. A sample tag code X for a sample is determined as described above, and stored within a memory location 14 of a computer. The sample tag code X is compared to the pointer file 12 for a matching sequence tag code. If a match is found, a pointer associated with the matching sequence tag code is used to access the corresponding sequence in the sequence database 10.

The pointer file 12 may be in any of several formats. In one format, each entry of the pointer file 12 comprises a tag code and a pointer to a corresponding record in the sequence database 12. The sample tag code X can be compared to sequence tag codes in a linear search. Alternatively, the sequence tag codes can be sorted and a binary search used. As another alternative, the sequence tag codes can be structured in a hierarchical tree structure (e.g., a B-tree), or as a singly or doubly linked list, or in any other conveniently searchable data structure or format.

In the preferred embodiment, each entry of the pointer file 12 comprises only a pointer to a corresponding record in the sequence database 10. In building the pointer file 12, each sequence tag code is assigned to an entry position in the pointer file 12 corresponding to the value of the tag code. For example, if a sequence tag code was "1043", a pointer to the corresponding record in the sequence database 10 would be stored in entry #1043 of the pointer file 12. The value of a sample tag code X can be used to directly address the location in the pointer file 12 that corresponds to the sample tag code X, and thus rapidly access the pointer stored in that location in order to address the sequence database 10.

Because only four values are needed to represent all possible base pairs, using binary coded decimal (BCD) numbers for tag codes in conjunction with the preferred pointer file 12 structure leads to a "sparse" pointer file 12 that wastes memory or storage space. Accordingly, the present invention transforms each tag code to number base 4 (i.e., 2 bits per code digit), in known fashion, resulting in a compact pointer file 12 structure. For example, for tag sequence "AGCT", with $A=00_2$, $C=01_2$, $G=10_2$, $T=11_2$, the base four representation in binary would be "00011011".

In contrast, the BCD representation would be "00000000 00000001 00000010 000000011". Of course, it should be understood that other mappings of base pairs to codes would provide equivalent function.

The concept of deriving a defined tag from a sample sequence in accordance with the present invention is also useful in comparing different samples for similarity. In the preferred embodiment, a computer method is used to match sequence tags from different samples. For example, in comparing materials having a large number of sequences (e.g., tissue), the frequency of occurrence of the various tags in a first sample can be mapped out as tag codes stored in a distribution or histogram-type data structure. For example, a table structured similar to pointer file 12 in FIG. 4 can be used where each entry comprises a frequency of occurrence value. Thereafter, the various tags in a second sample can be generated, converted to tag codes, and compared to the table by directly addressing table entries with the tag code. A count can be kept of the number of matches found, as well as the location of the matches, for output in text or graphic form on an output device, and/or for storage in a data storage system for later use.

The tag comparison aspects of the invention may be implemented in hardware or software, or a combination of both. Preferably, these aspects of the invention are implemented in computer programs executing on a programmable computer comprising a processor, a data storage system (including volatile and non-volatile memory and/or storage elements), at least one input device, and at least one output device. Data input through one or more input devices for temporary or permanent storage in the data storage system includes sequences, and may include previously generated tags and tag codes for known and/or unknown sequences. Program code is applied to the input data to perform the functions described above and generate output information. The output information is applied to one or more output devices, in known fashion.

Each such computer program is preferably stored on a storage media or device (e.g., ROM or magnetic diskette)

readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

The following examples are intended to illustrate but not limit the invention. While they are typical of those that might be used, other procedures known to those skilled in the art may alternatively be used.

EXAMPLES

For exemplary purposes, the SAGE method of the invention was used to characterized gene expression in the human pancreas. NlaIII was utilized as the first restriction endonuclease, or anchoring enzyme, and BsmFI as the second restriction endonuclease, or tagging enzyme, yielding a 9 bp tag (BsmFI was predicted to cleave the complementary strand 14 bp 3' to the recognition site GGGAC and to yield a 4 bp 5' overhang (New England BioLabs). Overlapping the BsmFI and NlaIII (CATG) sites as indicated (GGGA<u>CATG</u>) would be predicted to result in a 11 bp tag. However, analysis suggested that under the cleavage conditions used (37° C.), BsmFI often cleaved closer to its recognition site leaving a minimum of 12 bp 3' of its recognition site. Therefore, only the 9 bp closest to the anchoring enzyme site was used for analysis of tags. Cleavage at 65° C. results in a more consistent 11 bp tag.

Computer analysis of human transcripts from Gen Bank indicated that greater than 95% of tags of 9 bp in length were likely to be unique and that inclusion of two additional bases provided little additional resolution. Human sequences (84,300) were extracted from the GenBank 87 database using the Findseq program provided on the IntelliGenetics Bionet on-line service. All further analysis was performed with a SAGE program group written in Microsoft Visual Basic for the Microsoft Windows operating system. The SAGE database analysis program was set to include only sequences noted as "RNA" in the locus description and to exclude entries noted as "EST", resulting in a reduction to 13,241 sequences. Analysis of this subset of sequences using NlaIII as anchoring Enzyme indicated that 4,127 nine bp tags were unique while 1,511 tags were found in more than one entry. Nucleotide comparison of a randomly chosen subset (100) of the latter entries indicated that at least 83% were due to redundant data base entries for the same gene or highly related genes (>95% identity over at least 250 bp). This suggested that 5381 of the 9 bp tags (95.5%) were unique to a transcript or highly conserved transcript family. Likewise, analysis of the same subset of GenBank with an 11 bp tag resulted only in a 6% decrease in repeated tags (1511 to 1425) instead of the 94% decrease expected if the repeated tags were due to unrelated transcripts.

Example I

As outlined above, mRNA from human pancreas was used to generate ditags. Briefly, five ug mRNA from total pancreas (Clontech) was converted to double stranded cDNA using a BRL cDNA synthesis kit following the manufacturer's protocol, using the primer biotin-5'T$_{18}$-3'. The cDNA was then cleaved with NlaIII and the 3' restriction fragments isolated by binding to magnetic streptavidin beads (Dynal). The bound DNA was divided into two pools, and one of the following linkers ligated to each pool:

5'-TTTTACCAGCTTATTCAATTCGGTCCTCTCGCAC-AGGGACATG-3'
3'-<u>A</u>TGGTCGAATAAGTTAAGCCAGGAGAGCG-TGTCCCT-5' (SEQ ID NO:1 and 2)
5'-TTTTTGTAGACATTCTAGTATCTCGTCAAGTCG-GAAGGGACATG-3'
3'-<u>A</u>ACATCTGTAAGATCATAGAGCAGTTCAGC-CTTCCCT-5'(SEQ ID NO:3 and 4), where <u>A</u> is a dideoxy nucleotide (e.g., dideoxy A).

After extensive washing to remove unligated linkers, the linkers and adjacent tags were released by cleavage with BsmFI. The resulting overhangs were filled in with T4 polymerase and the pools combined and ligated to each other. The desired ligation product was then amplified for 25 cycles using 5'-CCAGCTTATTCAATTCGGTCC-3' and 5'-GTAGACATTCTAGTATCTCGT-3' (SEQ ID NO:5 and 6, respectively) as primers. The PCR reaction was then analyzed by polyacrylamide gel electrophoresis and the desired product excised. An additional 15 cycles of PCR were then performed to generate sufficient product for efficient ligation and cloning.

The PCR ditag products were cleaved with NlaIII and the band containing the ditags was excised and self-ligated. After ligation, the concatenated ditags were separated by polyacrylamide gel electrophoresis and products greater than 200 bp were excised. These products were cloned into the SphI site of pSL301 (Invitrogen). Colonies were screened for inserts by PCR using T7 and T3 sequences outside the cloning site as primers. Clones containing at least 10 tags (range 10 to 50 tags) were identified by PCR amplification and manually sequenced as described (Del Sal, et al. , *Biotechniques* 7:514, 1989) using 5'-GACGTCGACCTGAGGTAATTATAACC-3' (SEQ ID NO:7) as primer. Sequence files were analyzed using the SAGE software group which identifies the anchoring enzyme site with the proper spacing and extracts the two intervening tags and records them in a database. The 1,000 tags were derived from 413 unique ditags and 87 repeated ditags. The latter were only counted once to eliminate potential PCR bias of the quantitation. The function of SAGE software is merely to optimize the search for gene sequences.

Table 1 shows analysis of the first 1,000 tags. Sixteen percent were eliminated because they either had sequence ambiguities or were derived from linker sequences. The remaining 840 tags included 351 tags that occurred once and 77 tags that were found multiple times. Nine of the ten most abundant tags matched at least one entry in GenBank R87. The remaining tag was subsequently shown to be derived from amylase. All ten transcripts were derived from genes of known pancreatic function and their prevalence was consistent with previous analyses of pancreatic RNA using conventional approaches (Han, et al., *Proc. Natl. Acad. Sci. U.S.A.* 83:110, 1986; Takeda, et al., *Hum. Mol. Gen.,* 2:1793, 1993).

TABLE 1

Pancreatic SAGE Tags

| TAG | Gene | N | Percent |
|---|---|---|---|
| GAGCACACC | Procarboxypeptidase A1 (X67318) | 64 | 7.6 |
| TTCTGTGTG | Pancreatic Trypsinogen 2 (M27602) | 46 | 5.5 |
| GAACACAAA | Chymotrypsinogen (M24400) | 37 | 4.4 |
| TCAGGGTGA | Pancreatic Trypsin 1 (M22612) | 31 | 3.7 |
| GCGTGACCA | Elastase 111B (M18692) | 20 | 2.4 |
| GTGTGTGCT | Protease E (D00306) | 16 | 1.9 |
| TCATTGGCC | Pancreatic Lipase (M93285) | 16 | 1.9 |
| CCAGAGAGT | Procarboxypeptidase B (M81057) | 14 | 1.7 |
| TCCTCAAAA | No Match, See Table 2, P1 | 14 | 1.7 |
| AGCCTTGGT | Bile Salt Stimulated Lipase (X54457) | 12 | 1.4 |
| GTGTGCGCT | No Match | 11 | 1.3 |
| TGCGAGACC | No Match, See Table 2, P2 | 9 | 1.1 |
| GTGAAACCC | 21 Alu entries | 8 | 1.0 |
| GGTGACTCT | No Match | 8 | 1.0 |
| AAGGTAACA | Secretary Trypsin Inhibitor (M11949) | 6 | 0.7 |
| TCCCCTGTG | No Match | 5 | 0.6 |
| GTGACCACG | No Match | 5 | 0.6 |
| CCTGTAATC | M91159, M29366,11 Alu entries | 5 | 0.6 |
| CACGTTGGA | No Match | 5 | 0.6 |
| AGCCCTACA | No Match | 5 | 0.6 |
| AGCACCTCC | Elongation Factor 2 (Z11692) | 5 | 0.6 |
| ACGCAGGGA | No Match, See Table 2, P3 | 5 | 0.6 |
| AATTGAAGA | No Match, See Table 2, P4 | 5 | 0.6 |
| TTCTGTGGG | No Match | 4 | 0.5 |
| TTCATACAC | No Match | 4 | 0.5 |
| GTGGCAGGC | NF-kB(X61499), Mu entry (S94541) | 4 | 0.5 |
| GTAAAACCC | TNF receptor 11 (M55994), Alu entry (X01448) | 4 | 0.5 |
| GAACACACA | No Match | 4 | 0.5 |
| CCTGGGAAG | Pancreatic Mucin (J05582) | 4 | 0.5 |
| CCCATCGTC | Mitochondrial CytC Oxidase (X15759) | 4 | 0.5 |
| (SEQ ID NO:8–37) | | | |

| Summary | | | |
|---|---|---|---|
| SAGE tags Occurring | Greater than three times | 380 | 45.2 |
| | Three times (15 × 3=) | 45 | 5.4 |
| | Two times (32 × 2=) | 64 | 7.6 |
| | One time | 351 | 41.8 |
| | Total SAGE Tags | 840 | 100.0 |

"Tag" indicates the 9 bp sequence unique to each tag, adjacent to the 4 bp anchoring NlaIII site. "N" and "Percent" indicates the number of times the tag was identified and its frequency, respectively. "Gene" indicates the accession number and description of GenBank R87 entries found to match the indicated tag using the SAGE software group with the following exceptions. When multiple entries were identified because of duplicated entries, only one entry is listed. In the cases of chymotrypsinogen, and trypsinogen 1, other genes were identified that were predicted to contain the same tags, but subsequent hybridization and sequence analysis identified the listed genes as the source of the tags. "Alu entry" indicates a match with a GenBank entry for a transcript that contained at least one copy of the alu consensus sequence (Deininger, et al., *J Mol. Biol.*, 151:17, 1981).

Example 2

The quantitative nature of SAGE was evaluated by construction of an oligo-dT primed pancreatic cDNA library which was screened with cDNA probes for trypsinogen 1/2, procarboxpeptidase A1, chymotrypsinogen and elastase I-IIB/protease E. Pancreatic mRNA from the same preparation as used for SAGE in Example 1 was used to construct a cDNA library in the ZAP Express vector using the ZAP Express cDNA Synthesis kit following the manufacturer's protocol (Stratagene). Analysis of 15 randomly selected clones indicated that 100% contained cDNA inserts. Plates containing 250 to 500 plaques were hybridized as previously described (Ruppert, et al., *Mol. Cell. Biol.* 8:3104, 1988). cDNA probes for trypsinogen 1, trypsinogen 2, procarboxypeptidase A1, chymotrypsinogen, and elastase IIIB were derived by RT-PCR from pancreas RNA. The trypsinogen 1 and 2 probes were 93% identical and hybridized to the same plaques under the conditions used. Likewise, the elastase IIIB probe and protease E probe were over 95% identical and hybridized to the same plaques.

Figure 2:
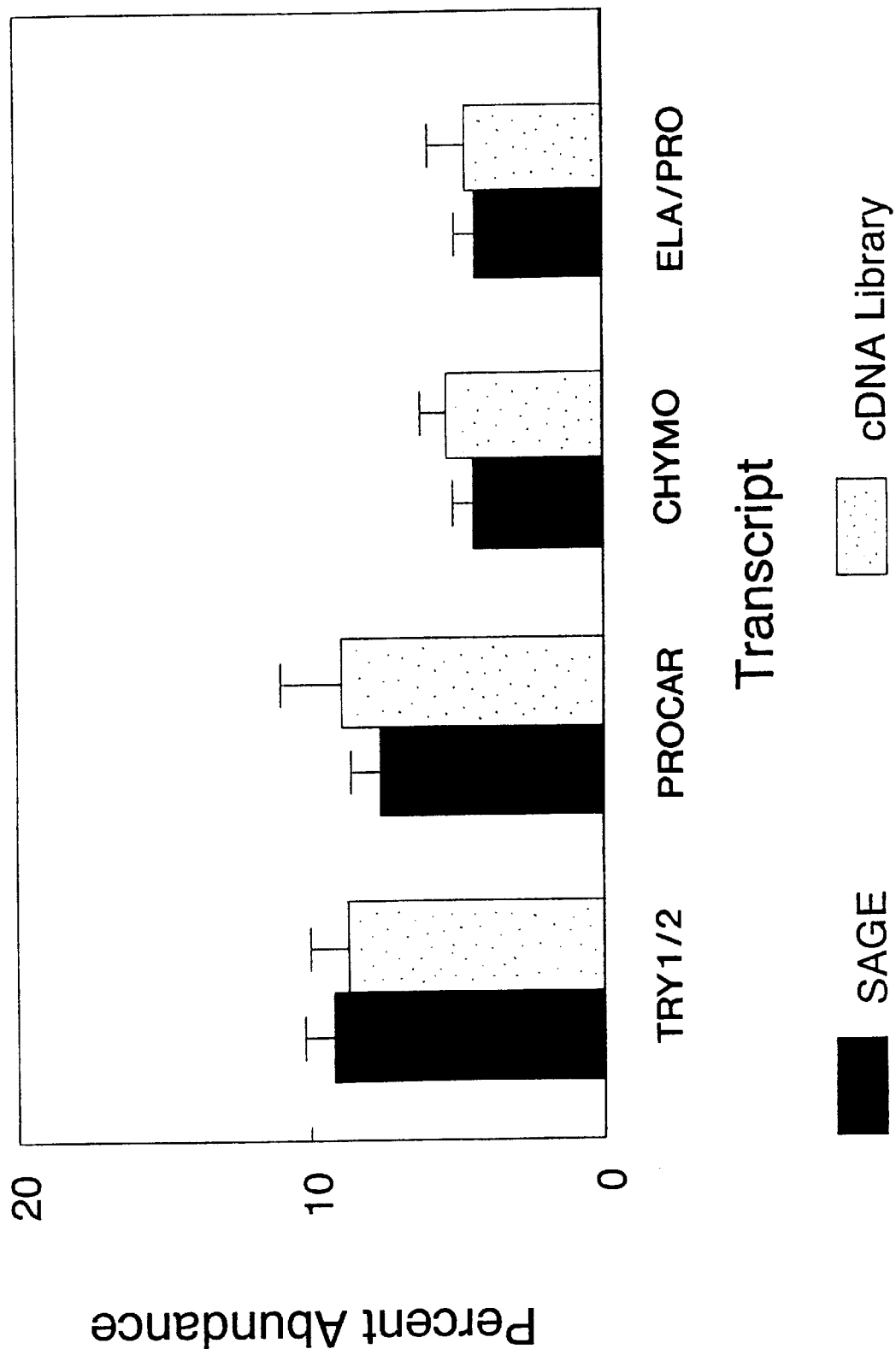
FIG. 2 shows a comparison of transcript abundance. Bars represent the percent abundance as determined by SAGE (dark bars) or hybridization analysis (light bars). SAGE quantitations were derived from Table 1 as follows: TRY 1/2 includes the tags for trypsinogen 1 and 2, PROCAR indicates tags for procarboxypeptidase A1, CHYMO indicates tags for chymotrypsinogen, and ELA/PRO includes the tags for elastase IIIB and protease E. Error bars represent the standard deviation determined by taking the square root of counted events and converting it to a percent abundance (assumed Poisson distribution).

The relative abundance of the SAGE tags for these transcripts was in excellent agreement with the results obtained with library screening (FIG. 2). Furthermore, whereas neither trypsinogen 1 and 2 nor elastase IIIB and protease E could be distinguished by the cDNA probes used to screen the library, all four transcripts could readily be distinguished on the basis of their SAGE tags (Table 1).

Example 3

Figure 3A:
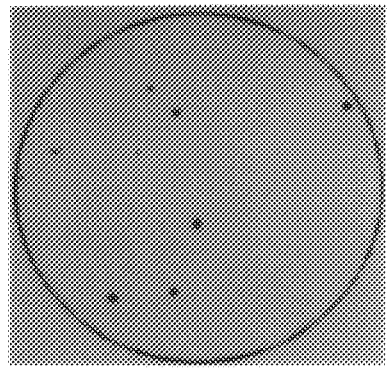
FIG. 3 shows the results of screening a cDNA library with SAGE tags. P1 and P2 show typical hybridization results obtained with 13 bp oligonucleotides as described in the Examples. P1 and P2 correspond to the transcripts described in Table 2. Images were obtained using a Molecular Dynamics PhosphorImager and the circle indicates the outline of the filter membrane to which the recombinant phage were transferred prior to hybridization.
Figure 3B:
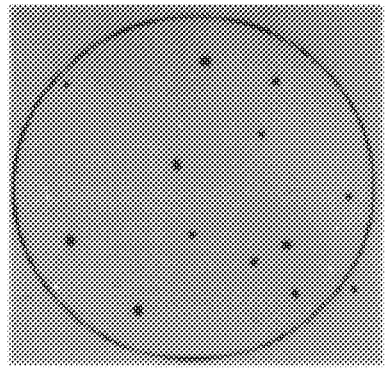

In addition to providing quantitative information on the abundance of known transcripts, SAGE could be used to identify novel expressed genes. While for the purposes of the SAGE analysis in this example, only the 9 bp sequence unique to each transcript was considered, each SAGE tag defined a 13 bp sequence composed of the anchoring enzyme (4 bp) site plus the 9 bp tag. To illustrate this potential, 13 bp oligonucleotides were used to isolate the transcripts corresponding to four unassigned tags (P1 to P4), that is, tags without corresponding entries from GenBank R87 (Table 1). In each of the four cases, it was possible to isolate multiple cDNA clones for the tag by simply screening the pancreatic cDNA library using 13 bp oligonucleotide as hybridization probe (examples in FIG. 3).

Plates containing 250 to 2,000 plaques were hybridized to oligonucleotide probes using the same conditions previously described for standard probes except that the hybridization temperature was reduced to room temperature. Washes were performed in 6×SSC/0.1% SDS for 30 minutes at room temperature. The probes consisted of 13 bp oligonucleotides which were labeled with $\gamma^{32}$P-ATP using T4 polynucleotide kinase. In each case, sequencing of the derived clones identified the correct SAGE tag at the predicted 3' end of the identified transcript. The abundance of plaques identified by hybridization with the 13-mers was in good agreement with that predicted by SAGE (Table 2). Tags P1 and P2 were found to correspond to amylase and preprocarboxypeptidase A2, respectively. No entry for preprocarboxypeptidase A2 and only a truncated entry for amylase was present in GenBank R87, thus accounting for their unassigned characterization. Tag P3 did not match any genes of known function in GenBank but did match numerous EST's, providing further evidence that it represented a bona fide transcript. The cDNA identified by P4 showed no significant homology, suggesting that it represented a previously uncharacterized pancreatic transcript.

TABLE 2

Characterization of Unassigned SAGE Tags

| TAG | Abundance SAGE | 13mer Hyb | SAGE Tag | Description |
|---|---|---|---|---|
| P1 TCCTCAAAA (SEQ ID NO:38) | 1.7% | 1.5% (6/388) | + | 3' end of Pancreatic Amylase (M28443) |
| P2 TGCGAGACC (SEQ ID NO:39) | 1.1% | 1.2% (43/3700) | + | 3' end of Preprocarboxypeptidase A2 (U19977) |
| P3 ACGCAGGGA (SEQ ID NO:40) | 0.6% | 0.2% (5/2772) | + | EST match (R45808) |
| P4 AATTGAAGA (SEQ ID NO:41) | 0.6% | 0.4% (6/1587) | + | no match |

"Tag" and "SAGE Abundance" are described in Table 1; "13mer Hyb" indicates the results obtained by screening a cDNA library with a 13mer, as described above. The number of positive plaques divided by the total plaques screened is indicated in parentheses following the percent abundance. A positive in the "SAGE Tag" column indicates that the expected SAGE tag sequence was identified near the 3' end of isolated clones. "Description" indicates the results of BLAST searches of the daily updated GenBank entries at NCBI a of Jun. 9, 1995 (Altschul, et al., *J Mol. Biol.*, 215:403, 1990). A description and Accession number are given for the most significant matches. P1 was found to match a truncated entry for amylase, and P2 was found to match an unpublished entry for preprocarboxypeptidase A2 which was entered after GenBank R87.

Example 4

Ditags produced by SAGE can be analyzed by PSA or CS, as described in the specification. In a preferred embodiment of PSA, the following steps are carried out with ditags:

Ditags are prepared, amplified and cleaved with the anchoring enzyme as described in the previous examples.

OOOOOOOOOOXXXXXXXXXXCATG-3'
3'-GTACOOOOOOOOOOXXXXXXXXXX

Four-base oligomers containing an identifier (e.g., a fluorescent moiety, FL) are prepared that are complementary to the overhangs, for example, FL-CATG. The FL-CATG oligomers (in excess) are ligated to the ditags as shown below:
5'-FL-CATGOOOOOOOOOOXXXXXXXXXXCATG
GTACOOOOOOOOOOXXXXXXXXXXGTAC-FL-5'

The ditags are then purified and melted to yield single-stranded DNAs having the formula:
5'-FL-CATGOOOOOOOOOOOXXXXXXXXXXCATG and GTACOOOOOOOOOOXXXXXXXXXXGTAC-FL-5', for example. The mixture of single-stranded DNAs is preferably serially diluted. Each serial dilution is hybridized under appropriate stringency conditions with solid matrices containing gridded single-stranded oligonucleotides; all of the oligonucleotides contain a half-site of the anchoring enzyme cleavage sequence. In the example used herein, the oligonucleotide sequences contain a CATG sequence at the 5' end:
CATGOOOOOOOOOO, CATGXXXXXXXXXX, etc.
(or alternatively a CATG sequence at the 3' end: OOOOOOOOOOCATG)

The matrices can be constructed of any material known in the art and the oligonucleotide-bearing chips can be generated by any procedure known in the art, e.g. silicon chips containing oligonucleotides prepared by the VLSIP procedure (Fodor et al., supra).

The oligonucleotide-bearing matrices are evaluated for the presence or absence of a fluorescent ditag at each position in the grid.

In a preferred embodiment, there are $4^{10}$, or 1,048,576, oligonucleotides on the grid(s) of the general sequence CATGOOOOOOOOOO, such that every possible 10-base sequence is represented 3' to the CATG, where CATG is used as an example of an anchoring enzyme half site that is complementary to the anchoring enzyme half site at the 3' end of the ditag. Since there are estimated to be no more than 100,000 to 200,000 different expressed genes in the human genome, there are enough oligonucleotide sequences to detect all of the possible sequences adjacent to the 3'-most anchoring enzyme site observed in the cDNAs from the expressed genes in the human genome.

In yet another embodiment, structures as described above containing the sequences PRIMER A- GGAGCATG $(X)_{10}$ $(O)_{10}$ CATGCATCC- PRIMER B PRIMER A- CCTCGTAC $(X)_{10}$ $(O)_{10}$ GTACGTAGG- PRIMER B are amplified, cleaved with tagging enzyme and thereafter with anchoring enzyme to generate tag complements of the structure: $(O)_{10}$ CATG-3', which can then be labeled, melted, and hybridized with oligonucleotides on a solid support.

A determination is made of differential expression by comparing the fluorescence profile on the grids at different dilutions among different libraries (representing differential screening probes). For example:

Library A, Ditags Diluted 1:10

|   | A | B | C | D | E |
|---|---|---|---|---|---|
| 1 | FL |   |   |   |   |
| 2 |   |   |   | FL |   |
| 3 |   | FL | FL |   |   |
| 4 |   |   |   | FL |   |
| 5 | FL |   |   |   |   |

Library B, Ditags Diluted 1:10

|   | A | B | C | D | E |
|---|---|---|---|---|---|
| 1 | FL |   |   |   |   |
| 2 |   |   | FL |   | FL |
| 3 |   | FL | FL |   |   |
| 4 |   |   |   |   |   |
| 5 | FL |   |   |   | FL |

Library A, Ditags Diluted 1:50

|   | A | B | C | D | E |
|---|---|---|---|---|---|
| 1 | FL |   |   |   |   |
| 2 |   |   |   |   |   |
| 3 |   | FL |   |   |   |
| 4 |   |   |   | FL |   |
| 5 | FL |   |   |   |   |

Library A, Ditags Diluted 1:100

|   | A | B | C | D | E |
|---|---|---|---|---|---|
| 1 | FL |   |   |   |   |
| 2 |   |   |   |   |   |
| 3 |   | FL |   |   |   |
| 4 |   |   |   | FL |   |
| 5 | FL |   |   |   |   |

Library B, Ditags Diluted 1:50

|   | A | B | C | D | E |
|---|---|---|---|---|---|
| 1 | FL |   |   |   |   |
| 2 |   | FL |   |   |   |

Library B, Ditags Diluted 1:100

|   | A | B | C | D | E |
|---|---|---|---|---|---|
| 1 | FL |   |   |   |   |
| 2 |   | FL |   |   |   |

-continued

| | | | | |
|---|---|---|---|---|
| 3 | FL | FL | 3 | FL |
| 4 | | | 4 | |
| 5 | | | 5 | |

The individual oligonucleotides thus hybridize to ditags with the following characteristics:

TABLE 3

| | 1:10 | | 1:50 | | 1:100 | |
|---|---|---|---|---|---|---|
| Dilution | Lib A | Lib B | Lib A | Lib B | Lib A | Lib B |
| 1A | + | + | + | + | + | + |
| 2C | | + | | + | | + |
| 2E | + | + | | | | |
| 3B | + | + | + | + | + | + |
| 3C | + | + | | + | | |
| 4D | + | | | + | | + |
| 5A | + | + | + | | + | |
| 5E | | + | | | | |

Table 3 summarizes the results of the differential hybridization. Tags hybridizing to 1A and 3B reflect highly abundant nRNAs that are not differentially expressed (since the tags hybridize to both libraries at all dilutions); tag 2C identifies a highly abundant mRNA, but only in Library B. 2E reflects a low abundance transcript (since it is only detected at the lowest dilution) that is not found to be differentially expressed; 3C reflects a moderately abundant transcript (since it is expressed at the lower two dilutions) in Library B that is expressed at low abundance in Library A. 4D reflects a differentially-expressed, high abundance transcript restricted to Library A; 5A reflects a transcript that is expressed at high abundance in Library A but only at low abundance in Library B; and 5E reflects a differentially-expressed transcript that is detectable only in Library B.

In another PSA embodiment, step 3 above does not involve the use of a fluorescent or other identifier; instead, at the last round of amplification of the ditags, labeled dNTPs are used so that after melting, half of all molecules are labeled and can serve as probes for hybridization to oligonucleotides fixed on the chips.

In yet another PSA embodiment, instead of ditags, a particular portion of the transcript is used, e.g., the sequence between the 3' terminus of the transcript and the first anchoring enzyme site. In that particular case, a double-stranded cDNA reverse transcript is generated as described in the Detailed Description. The transcripts are cut with the anchoring enzyme, a linker is added containing a PCR primer and amplification is initiated (using the primer at one end and the poly A tail at the other) while the transcripts are still on the strepavidin bead. At the last round of amplification, fluoresceinated dNTPs are used so that half of the molecules are labeled. The linker-primer can be optionally removed by use of the anchoring enzyme at this point in order to reduce the size of the fragments. The soluble fragments are then melted and captured on solid matrices containing CATGOOOOOOOOOO, as in the previous example. Analysis and scoring (only of the half of the fragments which contain fluoresceinated bases) is as described above.

For use in clonal sequencing, ditags or concatemers would be diluted and added to wells of multiwell plates, for example, or other receptacles so that on average the wells would contain, statistically, less than one DNA molecule per well (as is done in limited dilution for cell cloning). Each well would then receive reagents for PCR or another amplification process and the DNA in each receptacle would be sequenced, e.g., by mass spectroscopy. The results will either be a single sequence (there having been a single sequence in that receptacle), a "null" sequence (no DNA present) or a double sequence (more than one DNA molecule), which would be eliminated from consideration during data analysis. Thereafter, assessment of differential expression would be the same as described herein.

These results demonstrate that SAGE provides both quantitative and qualitative data about gene expression. The use of different anchoring enzymes and/or tagging enzymes with various recognition elements lends great flexibility to this strategy. In particular, since different anchoring enzymes cleave cDNA at different sites, the use of at least 2 different Aes on different samples of the same cDNA preparation allows confirmation of results and analysis of sequences that might not contain a recognition site for one of the enzymes.

As efforts to fully characterize the genome near completion, SAGE should allow a direct readout of expression in any given cell type or tissue. In the interim, a major application of SAGE will be the comparison of gene expression patterns in among tissues and in various developmental and disease states in a given cell or tissue. One of skill in the art with the capability to perform PCR and manual sequencing could perform SAGE for this purpose. Adaptation of this technique to an automated sequencer would allow the analysis of over 1,000 transcripts in a single 3 hour run. An ABI 377 sequencer can produce a 451 bp readout for 36 templates in a 3 hour run (45 lbp/11 bp per tag×36=1476 tags). The appropriate number of tags to be determined will depend on the application. For example, the definition of genes expressed at relatively high levels (0.5% or more) in one tissue, but low in another, would require only a single day. Determination of transcripts expressed at greater than 100 mRNA's per cell (0.025% or more) should be quantifiable within a few months by a single investigator. Use of two different Anchoring Enzymes will ensure that virtually all transcripts of the desired abundance will be identified. The genes encoding those tags found to be most interesting on the basis of their differential representation can be positively identified by a combination of data-base searching, hybridization, and sequence analysis as demonstrated in Table 2. Obviously, SAGE could also be applied to the analysis of organisms other than humans, and could direct investigation towards genes expressed in specific biologic states.

SAGE, as described herein, allows comparison of expression of numerous genes among tissues or among different states of development of the same tissue, or between pathologic tissue and its normal counterpart. Such analysis is useful for identifying therapeutically, diagnostically and prognostically relevant genes, for example. Among the many utilities for SAGE technology, is the identification of appropriate antisense or triple helix reagents which may be therapeutically useful. Further, gene therapy candidates can also be identified by the SAGE technology. Other uses include diagnostic applications for identification of individual genes or groups of genes whose expression is shown to correlate to predisposition to disease, the presence of disease, and prognosis of disease, for example. An abundance profile, such as that depicted in Table 1, is useful for the above described applications. SAGE is also useful for detection of an organism (e.g., a pathogen) in a host or detection of infection-specific genes expressed by a pathogen in a host.

The ability to identify a large number of expressed genes in a short period of time, as described by SAGE in the present invention, provides unlimited uses.

Although the invention has been described with reference to the presently preferred embodiment, it should be understood that various modifications can be made without departing from the spirit of the invention. Accordingly, the invention is limited only by the following claims.

---

What is claimed is:

1. An isolated oligonucleotide composition derived from cDNA, said composition comprising:
at least two different defined nucleotide sequence tags, wherein each defined nucleotide sequence tag consists of about 6 to 30 nucleotides of said cDNA 5' of the 5'-most cleavage site of a restriction endonuclease within said cDNA or 3' of the 3'-most cleavage site of a restriction endonuclease within said cDNA;
wherein at least one tag corresponds to at least one expressed gene.

2. The composition of claim 1, wherein at least two of said tags are joined tail-to-tail to form a ditag, wherein said tail of said tag is distalmost to said cleavage site within said cDNA and wherein the oligonucleotide consists of about 1 to 200 ditags.

3. The composition of claim 2, wherein the oligonucleotide consists of about 8 to 20 ditags.

4. A method for the detection of gene expression comprising:
providing complementary deoxyribonucleic acid (cDNA) oligonucleotides;
cleaving said cDNA oligonucleotides with a restriction enzyme at a first restriction endonuclease site to provide cDNA fragments;
isolating the 5' or 3' end of said cDNA fragments to provide defined nucleotide sequence tags to said oligonucleotides of said fragments;
isolating a first define nucleotides sequence tag from a first cDNA oligonucleotides and second defined nucleotide sequence tag from a second cDNA oligonucleotides;
linking the first tag to a first oligonucleotides linker, wherein the first oligonucleotides linker comprises a first sequence for hybridization of an amplification primer and linking the second tag to a second tag to a second oligonucleotides linker, wherein the second oligonucleotides linker comprises a second sequence for hybridization of an amplification primer; and
determining the nucleotide sequence of a tag, wherein said tag corresponds to an expressed gene.

5. The method of claim 4, further comprising ligating the first tag linked to the first oligonucleotide linker to the second tag linked to the second oligonucleotide linker and forming a ditag.

6. The method of claim 5, further comprising amplifying the ditag oligonucleotide.

7. The method of claim 5, further comprising producing concatemers of the ditags.

8. The method of claim 7, wherein the concatemer consists of about 2 to 200 ditags.

9. The method of claim 8, wherein the concatemer consists of about 8 to 20 ditags.

10. The method of claim 4, wherein the first and second oligonucleotide linkers comprise the same nucleotide sequence.

11. The method of claim 4, wherein the first and second oligonucleotide linkers comprise different nucleotide sequences.

12. The method of claim 11, wherein the first and second oligonucleotide linkers have a sequence:
5'-TTTTACCAGCTTATTCAATTCGGTCCTCTCGCAC-AGGGACATG-3' (SEQ ID NO:1)
3'-ATGGTCGAATAAGTTAAGCCAGGAGAGCGT-GTCCCT-5' (SEQ ID NO:2)
or
5'-TTTTTGTAGACATTCTAGTATCTCGTCAAGTCGG-AAGGGACATG-3' (SEQ ID NO:3)
3'-AACATCTGTAAGATCATAGAGCAGTTCAG-CCTTCCCT-5' (SEQ ID NO:4)

wherein A is dideoxy A.

13. The method of claim 4, wherein the linkers comprise a second restriction endonuclease recognition site which allows cleavage at a site distant from the recognition site.

14. The method of claim 13, wherein the second restriction endonuclease is a type IIS endonuclease.

15. The method of claim 14, wherein the type IIS endonuclease is selected from the group consisting of BsmFI and FokI.

16. The method of claim 5, wherein the ditag is about 12 to 60 base pairs.

17. The method of claim 16, wherein the ditag is about 18 to 22 base pairs.

18. The method of claim 6, wherein the amplifying is by polymerase chain reaction (PCR).

19. The method of claim 18, wherein primers for PCR are selected from the group consisting of
5'-CCAGCTTATTCAATTCGGTCC-3' (SEQ ID NO:5) and
5'-GTAGACATTCTAGTATCTCGT-3' (SEQ ID NO:6).

20. A method for detection of gene expression comprising:
  cleaving a cDNA sample with a first restriction endonuclease, wherein the endonuclease cleaves the cDNA at a defined position at the 5' or 3' terminus of the cDNA thereby producing defined sequence tags;
  isolating the defined sequence tags;
  dividing said defined sequence tags into first and second pools;
  ligating a first pool of tags with a first oligonucleotide linker having a first sequence capable of hybridizing to an amplification primer and ligating a second pool of tags with a second oligonucleotide linker having a second sequence capable of hybridizing to an amplification primer;
  cleaving the tags with a second restriction endonuclease which cleaves at a position outside its recognition sequence;
  ligating the two pools of tags to produce a ditag; and
  determining the nucleotide sequence of the tag(s), wherein the tag(s) correspond to a mRNA from an expressed gene.

21. The method of claim 20, further comprising amplifying the ditag.

22. The method of claim 20, wherein the first restriction endonuclease has at least one recognition site in the cDNA.

23. The method of claim 22, wherein the first restriction enzyme has a four base pair recognition site.

24. The method of claim 23, wherein the restriction endonuclease is NlaIII.

25. The method of claim 20, wherein the cDNA comprises a means for capture.

26. The method of claim 25, wherein the means for capture is a binding element.

27. The method of claim 26, wherein the binding element is biotin.

28. The method of claim 20, wherein the first and second oligonucleotide linkers comprise the same nucleotide sequence.

29. The method of claim 20, wherein the first and second oligonucleotide linkers comprise different nucleotide sequences.

30. The method of claim 29, wherein the first and second oligonucleotide linkers have a sequence;

5'-TTTTACCAGCTTATTCAATTCGGTCCTCTCGCA-CAGGGACATG-3' (SEQ ID NO:1)
3'-ATGGTCGAATAAGTTAAGCCAGGAGAGCG-TGTCCCT-5' (SEQ ID NO:2)
or
5'-TTTTTGTAGACATTCTAGTATCTCGTCAAGTCG-GAAGGGACATG-3' (SEQ ID NO:3)
3'-AACATCTGTAAGATCATAGAGCAGTTCAGC-CTTCCCT-5' (SEQ ID NO:4)
wherein A is dideoxy A.

31. The method of claim 20, wherein the second restriction endonuclease is a type IIS endonuclease.

32. The method of claim 31, wherein the type IIS endonuclease is selected from the group consisting of BsmFI and FokI.

33. The method of claim 20, wherein the ditag is about 12 to 60 base pairs.

34. The method of claim 34, wherein the ditag is about 14 to 22 base pairs.

35. The method of claim 20, further comprising ligating the ditags to produce a concatemer.

36. The method of claim 35, wherein the concatemer consists of about 2 to 200 ditags.

37. The method of claim 36, wherein the concatemer consists of about 8 to 20 ditags.

38. The method of claim 20, wherein the amplifying is by polymerase chain reaction (PCR).

39. The method of claim 38, wherein primers for PCR are selected from the group consisting of
5'-CCAGCTTATTCAATTCGGTCC-3' (SEQ ID NO:5) and
5'-GTAGACATTCTAGTATCTCGT-3' (SEQ ID NO:6).

40. A kit useful for detection of gene expression wherein the presence of a cDNA ditag is indicative of expression of a gene having a sequence of a tag of the ditag, the kit comprising a first container containing a first oligonucleotide linker having a first hybridization sequence which hybridizes an amplification primer; a second container containing a second oligonucleotide linkers having a second hybridization sequence which hybridizes to an amplification primer, wherein the linkers further comprise a restriction endonuclease recognition site; and third and fourth containers having nucleic acid primers for hybridization to the first and second hybridization sequences of the linkers.

41. The kit of claim 40, wherein the linkers have a sequence
5'-TTTTACCAGCTTATTCAATTCGGTCCTCTCGCAC-AGGGACATG-3' (SEQ ID NO:1)
3'-ATGGTCGAATAAGTTAAGCCAGGAGAGC-GTGTCCCT-5' (SEQ ID NO:2)
or
5'-TTTTTGTAGACATTCTAGTATCTCGTCAAGTCG-GAAGGGACATG-3' (SEQ ID NO:3)
3'-AACATCTGTAAGATCATAGAGCAGTTCAGC-CTTCCCT-5' (SEQ ID NO:4)
wherein A is dideoxy A.

42. The kit of claim 40, wherein the restriction endonuclease is a type IIS endonuclease.

43. The kit of claim 42, wherein the type IIS endonuclease is BsmFI.

44. The kit of claim 40, wherein the primers for amplification are selected from the group consisting of
5'-CCAGCTTATTCAATTCGGTCC-3' (SEQ ID NO:5) and
5'-GTAGACATTCTAGTATCTCGT-3' (SEQ ID NO:6).

* * * * *

UNITED STATES PATENT AND TRADEMARK OFFICE
CERTIFICATE OF CORRECTION

PATENT NO. : 5,866,330
APPLICATION NO. : 08/544861
DATED : February 2, 1999
INVENTOR(S) : Kenneth W. Kinzler et al.

It is certified that error appears in the above-identified patent and that said Letters Patent is hereby corrected as shown below:

In Claim 4, Column 21, Line 62:
    Please delete "define" and insert --defined--

In Claim 4, Column 21, Line 62:
    Please delete "nucleotides" and insert --nucleotide--

In Claim 4, Column 21, Line 63:
    Please delete "oligonucleotides" and insert --oligonucleotide--

In Claim 4, Column 21, Line 63:
    Please insert --a-- after "and" and before "second"

In Claim 4, Column 21, Line 64:
    Please delete "oligonucleotides" and insert --oligonucleotide--

In Claim 4, Column 21, Line 66:
    Please delete "oligonucleotides" and insert --oligonucleotide--

In Claim 4, Column 21, Line 67:
    Please delete "oligonucleotides" and insert --oligonucleotide--

In Claim 4, Column 22, Line 35:
    Please delete "a second tag to"

In Claim 4, Column 22, Line 36:
    Please delete "oligonucleotides" and insert --oligonucleotide--

UNITED STATES PATENT AND TRADEMARK OFFICE
CERTIFICATE OF CORRECTION

PATENT NO. : 5,866,330
APPLICATION NO. : 08/544861
DATED : February 2, 1999
INVENTOR(S) : Kenneth W. Kinzler et al.

It is certified that error appears in the above-identified patent and that said Letters Patent is hereby corrected as shown below:

In Claim 4, Column 22, Line 37:
 Please delete "oligonucleotides" and insert --oligonucleotide--

Signed and Sealed this

Thirty-first Day of March, 2009

JOHN DOLL
*Acting Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 43 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:1:

TTTTACCAGC TTATTCAATT CGGTCCTCTC GCACAGGGAC ATG 43

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:2:

ATGGTCGAAT AAGTTAAGCC AGGAGAGCGT GTCCCT 36

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:3:

TTTTTGTAGA CATTCTAGTA TCTCGTCAAG TCGGAAGGGA CATG 44

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:4:

AACATCTGTA AGATCATAGA GCAGTTCAGC CTTCCCT 37

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:5:

CCAGCTTATT CAATTCGGTC C                                                          21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:6:

GTAGACATTC TAGTATCTCG T                                                          21

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:7:

GACGTCGACC TGAGGTAATT ATAACC                                                     26